(12) United States Patent
Wiebe et al.

(10) Patent No.: US 8,846,793 B2
(45) Date of Patent: Sep. 30, 2014

(54) PROCESS

(75) Inventors: Lars Wiebe, Grindsted (DK); Thomas Schmidt, Grindsted (DK)

(73) Assignee: Dupont Nutrition Biosciences APS, Copenhagen (DK)

( * ) Notice: Subject to any disclaimer, the term of this patent is extended or adjusted under 35 U.S.C. 154(b) by 250 days.

(21) Appl. No.: 13/391,355

(22) PCT Filed: Aug. 19, 2010

(86) PCT No.: PCT/IB2010/002992
§ 371 (c)(1),
(2), (4) Date: Apr. 26, 2012

(87) PCT Pub. No.: WO2011/021107
PCT Pub. Date: Feb. 24, 2011

(65) Prior Publication Data
US 2012/0214919 A1 Aug. 23, 2012

(30) Foreign Application Priority Data

Aug. 20, 2009 (GB) .................................. 0914572.3

(51) Int. Cl.
| | | |
|---|---|---|
| C08K 5/10 | (2006.01) | |
| C07C 59/185 | (2006.01) | |
| C07C 67/04 | (2006.01) | |
| C07C 67/08 | (2006.01) | |
| C07C 69/67 | (2006.01) | |
| C11C 3/00 | (2006.01) | |
| C08K 5/103 | (2006.01) | |
| C07C 67/31 | (2006.01) | |

(52) U.S. Cl.
CPC ................ *C07C 67/08* (2013.01); *C07C 67/04* (2013.01); *C07C 69/67* (2013.01); *C11C 3/00* (2013.01); *C08K 5/103* (2013.01); *C07C 67/31* (2013.01)
USPC .......................................... 524/311; 554/122

(58) Field of Classification Search
USPC ....................................................... 524/311
See application file for complete search history.

(56) References Cited

U.S. PATENT DOCUMENTS

| | | | |
|---|---|---|---|
| 2,879,281 A | 3/1959 | Brokaw | |
| 4,426,477 A | 1/1984 | Yasumatsu et al. | |
| 2005/0090590 A1* | 4/2005 | Nielsen et al. | 524/287 |
| 2006/0276575 A1* | 12/2006 | Hamaguchi et al. | 524/308 |

FOREIGN PATENT DOCUMENTS

| | | |
|---|---|---|
| EP | 1 029 890 | 8/2000 |
| EP | 1 218 443 | 7/2002 |
| EP | 1728818 A1 | 12/2006 |
| WO | WO 0114466 A1 | 3/2001 |
| WO | WO 2006108754 | 10/2006 |
| WO | WO 2008081332 A1 | 7/2008 |

OTHER PUBLICATIONS

Wiebe L., Sustainable Plasticisers, 101st AOCS Annual Meeting & Expo, Phoenix AZ, May 16-19, 2010.
DIN 53457 Determination of the elastic modulus by tensile, compression and bend testing, Oct. 1987.
DIN 53505 Shore A and Shore D hardness testing of rubber, Aug. 2000.

(Continued)

*Primary Examiner* — Hui Chin
(74) *Attorney, Agent, or Firm* — Steptoe & Johnson LLP

(57) ABSTRACT

A process for the preparation of a compound can have the formula

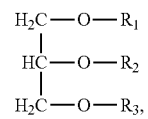

wherein $R_1$, $R_2$ and $R_3$ are independently selected from hydrogen and acyl groups, wherein at least one of $R_1$, $R_2$ and $R_3$ is a branched chain long acyl group of the formula

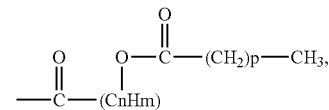

wherein n is from 9 to 21 and m is 2n, and wherein p is from 0 to 4, wherein the other of $R_1$, $R_2$ and $R_3$ are selected from short acyl groups of the formula

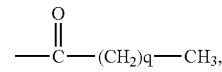

wherein q is from 0 to 4; the process comprising the steps of:
(1) providing an unsaturated compound having the formula

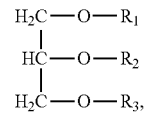

(2) if at least one of $R_1$, $R_2$ and $R_3$ is hydrogen, optionally acylating the compound; and (3a) (i) hydroxylating the unsaturated long acyl group and (ii) acylating the hydroxy long acyl group, or (3b) reacting the unsaturated long acyl group with a carboxylic acid.

43 Claims, 2 Drawing Sheets

(56) References Cited

OTHER PUBLICATIONS

Nolan-ITU Pty Ltd "Biodegradable Plastics—Developments and Environmental Impacts", Oct. 2002, by Australian Government Department of the Environment and Heritage (http://www.deh.gov.au/settlements/publications/waste/degradables/biodegradable/chapter3.html).

International Preliminary Report on Patentability and the Written Opinion dated Mar. 1, 2012 for PCT/IB2010/002992.
Database Reaxys [Online]; Elsevier Properties SA, XP-002650838, Database accession No. 6931468 abstract, Ozaki: Proceedings of the Imperial Academy (Tokyo), vol. 2, 1926, p. 341.
Database Reaxys [Online]; Elsevier Properties SA, XP-002650839, Database accession No. 17861 abstract, Nasini; Mattei; Kolloid-Zeitschrift, vol. 101, 1942, p. 116.

* cited by examiner

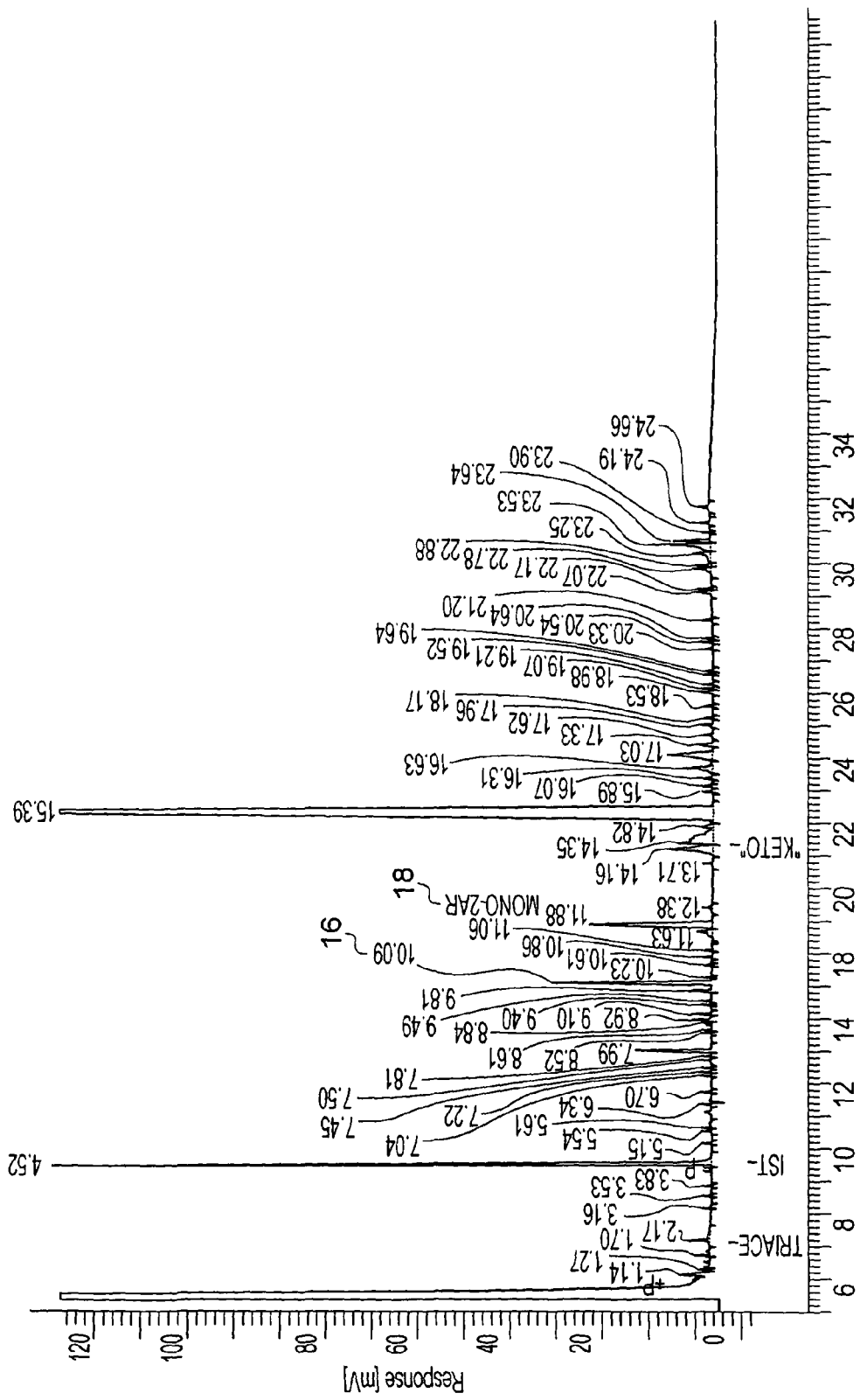
Figure 1 GC chromatogram of distilled reaction product

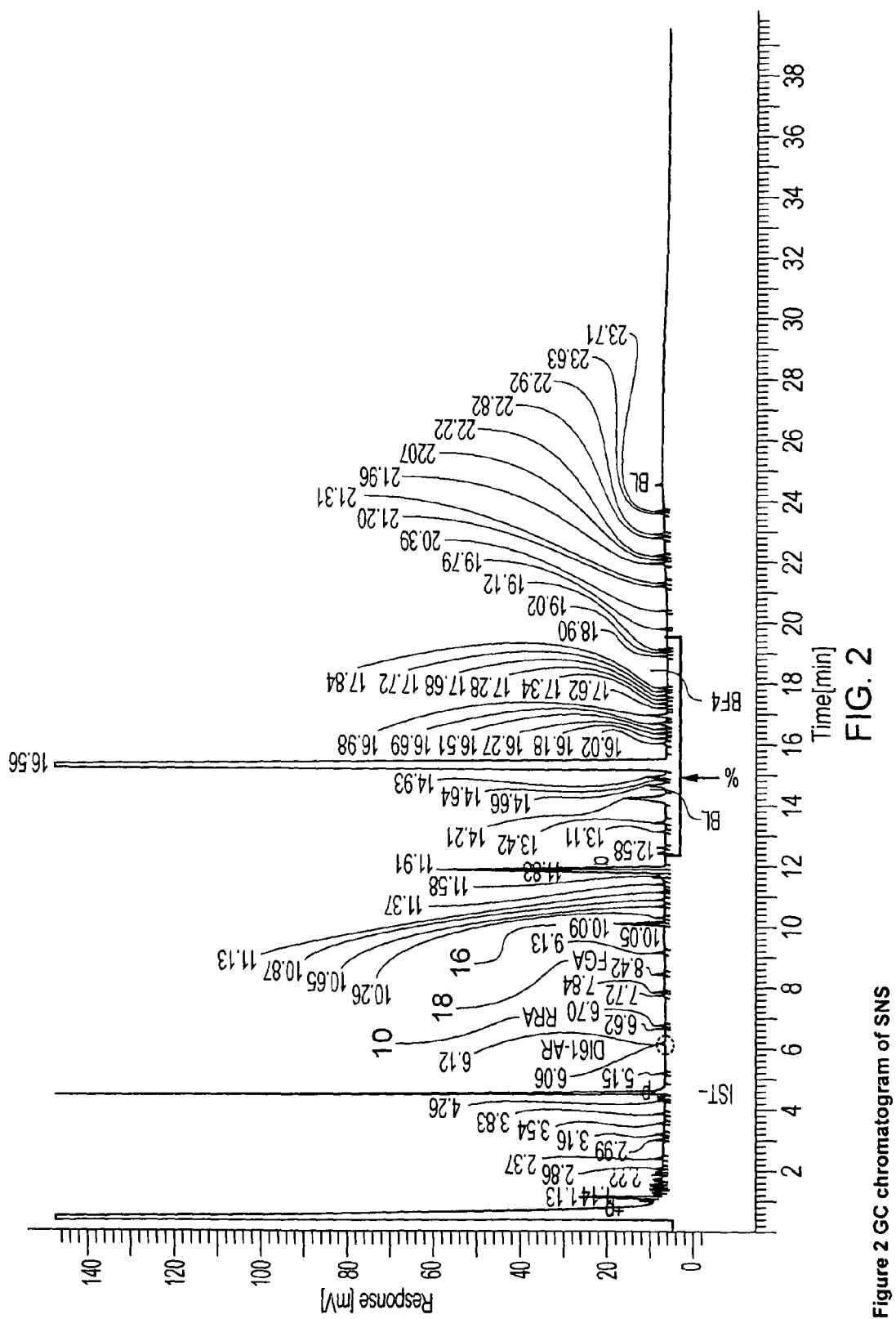
Figure 2 GC chromatogram of SNS

PROCESS

CLAIM FOR PRIORITY

This application claims priority under 35 USC 371 to International Application No. PCT/IB2010/002992, filed on Aug. 19, 2010, which claims priority to British Application No. 0914572.3, filed on Aug. 20, 2009, each of which is hereby incorporated by reference in its entirety.

The present invention relates to a process. In particular, the present invention relates to a process for preparing a compound that may be used in polymers, for example as a plasticiser or impact modifier, a compound made by that process, and a composition comprising a polymer and the compound.

The manufacturing properties of thermoplastic polymers, for example the extruding properties of such polymers, is often modified/enhanced by the addition of plasticisers thereto. As acknowledged in the prior art, such as in U.S. Pat. No. 4,426,477, there is a tendency toward avoiding the commonly used plasticisers such as dioctyl adipate (DOA) and phthalate plasticisers such as dioctyl phthalate (DOP). The safety of these plasticisers has been called into question, particularly in certain applications.

The problems of phthalate plasticisers are addressed in, for example WO01/14466. WO01/14466 relates to materials such as compounds of the formula.

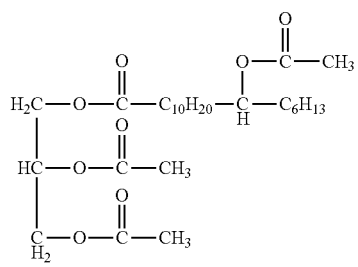

This compound is sold by Danisco A/S as SOFT N SAFE and has met with commercial success. WO01/14466 teaches a number of routes for preparing the disclosed compounds. Two of these routes are summarized in the schemes below

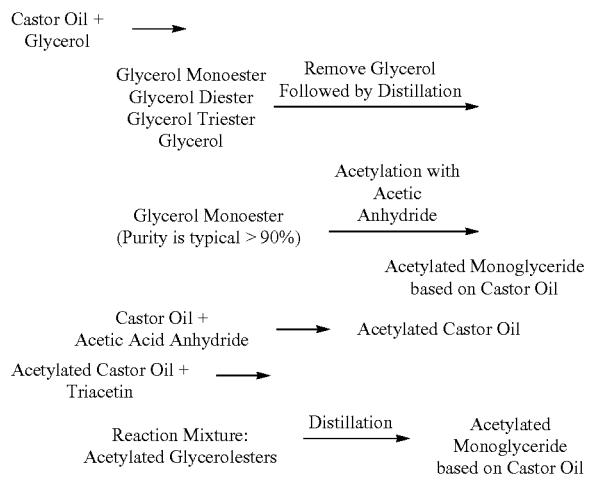

Although these routes adequately provide a product with the desired functionality, they are limited as to the position of the acyl branch group on the long fatty acid chain. For example, in the case of castor oil, the hydroxy group at position 12 determines that acylation will occur here. The requirement that a hydroxy group be present on the long fatty acid chain also limits the starting oils that be used in the process of WO01/14466.

In a first aspect the present invention provides a process for the preparation of a compound having the formula

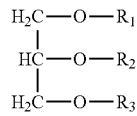

wherein $R_1$, $R_2$ and $R_3$ are independently selected from hydrogen and acyl groups, wherein at least one of $R_1$, $R_2$ and $R_3$ is a branched chain long acyl group of the formula

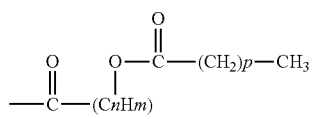

wherein n is from 9 to 21 and m is 2n, and wherein p is from 0 to 4 wherein the other of $R_1$, $R_2$ and $R_3$ are selected from short acyl groups of the formula wherein q is from 0 to 4

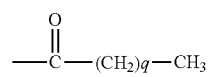

the process comprising the steps of:

(1) providing an unsaturated compound having the formula

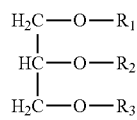

wherein $R_1$, $R_2$ and $R_3$ are independently selected from
  (a) hydrogen,
  (b) unsaturated long acyl group of the formula

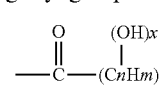

wherein x is from 0 to 3, and wherein n is from 9 to 21 and m is 2n−1−x, 2n−3−x or 2n−5−x; and (c) short acyl groups of the formula
wherein q is from 0 to 4

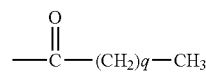

wherein at least one of $R_1$, $R_2$ and $R_3$ is an unsaturated long acyl group; and (2) if at least one of $R_1$, $R_2$ and $R_3$ is hydrogen, optionally acylating the compound; and (3a) (i) hydroxylating the unsaturated long acyl group, to provide a hydroxy long acyl group of the formula

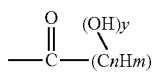

wherein y is from 1 to 4, n is from 9 to 21 and m is $2n+1-y$, $2n-1-y$ or $2n-3-y$, and (ii) acylating the hydroxy long acyl group to provide a branched long acyl group of the formula

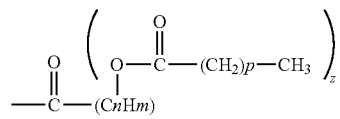

wherein z is from 1 to 4, n is from 9 to 21 and m is $2n+1-z$, $2n-1-z$ or $2n-3-z$, and wherein p is from 0 to 4;
or (3b) reacting the unsaturated long acyl group with a carboxylic acid of the formula

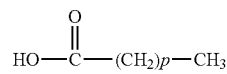

to provide a branched long acyl group of the formula

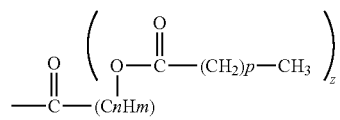

wherein z is from 1 to 4, n is from 9 to 21 and m is $2n+1-z$, $2n-1-z$ or $2n-3-z$, and wherein p is from 0 to 4.

In a second aspect the present invention provides a compound obtained or obtainable by a process as defined herein.

In a third aspect the present invention provides a compound selected from compounds of the formulae

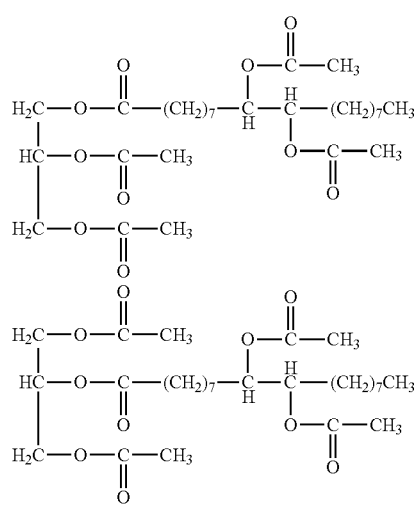

-continued

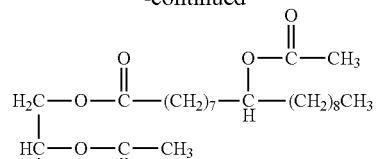

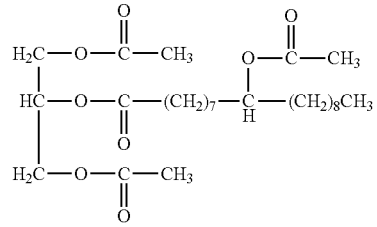

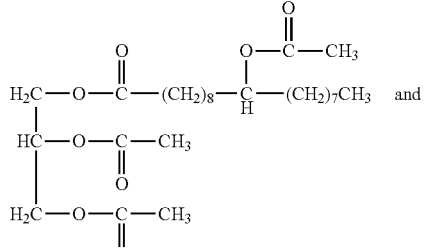

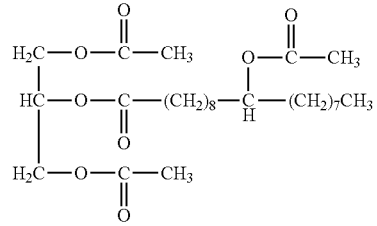

and

In a fourth aspect the present invention provides a composition comprising i) a polymer; and ii) a compound as defined herein.

For ease of reference these and further aspects of the present invention are now discussed under appropriate section headings. However, the teachings under each section are not necessarily limited to each particular section.

DETAILED DESCRIPTION

As discussed herein, the present process requires steps (1) and (2), and (3a) or (3b).

In one aspect steps (1), (2) and (3a) are performed. In this aspect, the present invention provides process for the preparation of a compound having the formula

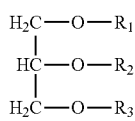

wherein $R_1$, $R_2$ and $R_3$ are independently selected from hydrogen and acyl groups, wherein at least one of $R_1$, $R_2$ and $R_3$ is a branched chain long acyl group of the formula

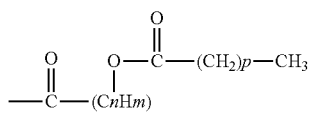

wherein n is from 9 to 21 and m is 2n, and wherein p is from 0 to 4 wherein the other of $R_1$, $R_2$ and $R_3$ are selected from short acyl groups of the formula wherein q is from 0 to 4

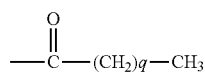

the process comprising the steps of:

(1) providing an unsaturated compound having the formula

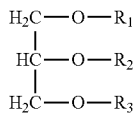

wherein $R_1$, $R_2$ and $R_3$ are independently selected from
(a) hydrogen,
(b) unsaturated long acyl group of the formula

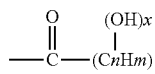

wherein x is from 0 to 3, and wherein n is from 9 to 21 and m is 2n−1−x, 2n−3−x or 2n−5−x; and (c) short acyl groups of the formula wherein q is from 0 to 4

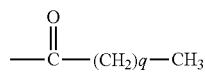

wherein at least one of $R_1$, $R_2$ and $R_3$ is an unsaturated long acyl group; and (2) if at least one of $R_1$, $R_2$ and $R_3$ is hydrogen, optionally acylating the compound; and (3a) (i) hydroxylating the unsaturated long acyl group, to provide a hydroxy long acyl group of the formula

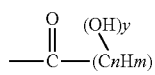

wherein y is from 1 to 4, n is from 9 to 21 and m is 2n+1−y, 2n−1−y or 2n−3−y, and (ii) acylating the hydroxy long acyl group to provide a branched long acyl group of the formula

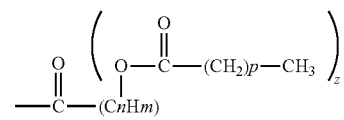

wherein z is from 1 to 4, n is from 9 to 21 and m is 2n+1−z, 2n−1−z or 2n−3−z, and wherein p is from 0 to 4.

In one aspect steps (1), (2) and (3b) are performed. In this aspect, the present invention provides process for the preparation of a compound having the formula

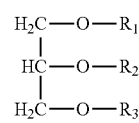

wherein $R_1$, $R_2$ and $R_3$ are independently selected from hydrogen and acyl groups, wherein at least one of $R_1$, $R_2$ and $R_3$ is a branched chain long acyl group of the formula

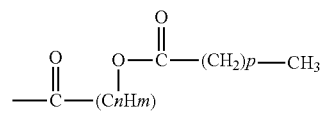

wherein n is from 9 to 21 and m is 2n, and wherein p is from 0 to 4 wherein the other of $R_1$, $R_2$ and $R_3$ are selected from short acyl groups of the formula

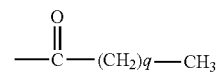

wherein q is from 0 to 4 the process comprising the steps of:

(1) providing an unsaturated compound having the formula

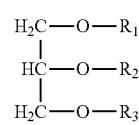

wherein $R_1$, $R_2$ and $R_3$ are independently selected from
(a) hydrogen,
(b) unsaturated long acyl group of the formula

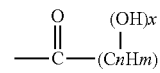

wherein x is from 0 to 3, and wherein n is from 9 to 21 and m is 2n−1−x, 2n−3−x or 2n−5−x; and (c) short acyl groups of the formula

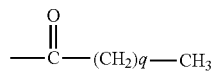

wherein q is from 0 to 4 wherein at least one of $R_1$, $R_2$ and $R_3$ is an unsaturated long acyl group; and (2) if at least one of $R_1$, $R_2$ and $R_3$ is hydrogen, optionally acylating the compound; and (3b) reacting the unsaturated long acyl group with a carboxylic acid of the formula

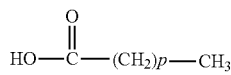

to provide a branched long acyl group of the formula

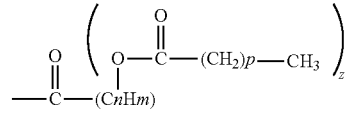

wherein z is from 1 to 4, n is from 9 to 21 and m is $2n+1-z$, $2n-1-z$ or $2n-3-z$, and wherein p is from 0 to 4.

In one aspect, step (2) of the process, namely optionally acylating the compound if at least one of $R_1$, $R_2$ and $R_3$ is hydrogen, is performed. In this aspect, step (2) requires acylating the compound if at least one of $R_1$, $R_2$ and $R_3$ is hydrogen.

In one aspect, step (2) of the process, namely optionally acylating the compound if at least one of $R_1$, $R_2$ and $R_3$ is hydrogen, is not performed. In this aspect, step (2) is omitted.

As discussed herein, the present invention provides among other things a compound having the formula

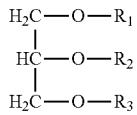

wherein $R_1$, $R_2$ and $R_3$ are independently selected from hydrogen and acyl groups, wherein at least one of $R_1$, $R_2$ and $R_3$ is a branched chain long acyl group of the formula

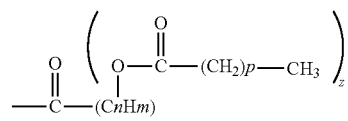

wherein z is from 1 to 4, n is from 9 to 21, m is $2n+1-z$ or $2n-1-z$, and wherein p is from 0 to 4.

The compound is derived from an unsaturated compound having the formula

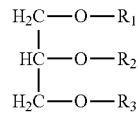

wherein $R_1$, $R_2$ and $R_3$ are independently selected from hydrogen, unsaturated long acyl group of the formula

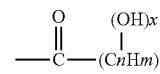

wherein x is from 0 to 3, and wherein n is from 9 to 21 and m is $2n-1-x$, $2n-3-x$ or $2n-5-x$; and
and short acyl groups of the formula
wherein q is from 0 to 4

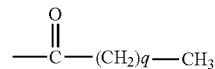

wherein at least one of $R_1$, $R_2$ and $R_3$ is an unsaturated long acyl group. The unsaturated long acyl group is hydroxylated to provide a hydroxy long acyl group of the formula

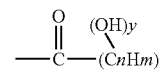

wherein y is from 1 to 4, n is from 9 to 21 and m is $2n+1-y$, $2n-1-y$ or $2n-3-y$ In one preferred aspect in respect of the unsaturated long acyl group n is from 9 to 21 and m is $2n-1-x$. In this aspect, for the hydroxy long acyl group 11 is from 9 to 21 and m is $2n+1-y$.

In a preferred aspect a compound having the formula is prepared

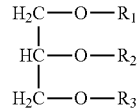

wherein two of $R_1$, $R_2$ and $R_3$ are the short acyl groups and one of $R_1$, $R_2$ and $R_3$ is a branched long acyl group. In this aspect, $R_1$ and $R_2$ may be a short acyl groups and $R_3$ is a branched long acyl group. In this aspect, $R_1$ and $R_3$ may be a short acyl groups and $R_2$ is a branched long acyl group. In this aspect, $R_2$ and $R_3$ may be a short acyl groups and $R_1$ is a branched long acyl group.

The value of n, which denotes the length of long acyl chain may be chosen as required. In a preferred aspect n is from 13 to 19. Preferably n is from 15 to 19. In a highly preferred aspect n is 17. When n is 17, the long acyl chain is derived from a C18 fatty acid. A particularly preferred long acyl chain is derived from oleic acid.

The value of p, which denotes the length of branch on the long acyl chain may be chosen as required. In a preferred aspect p is 0 to 3. In a highly preferred aspect p is 0 or 1. In a further highly preferred aspect p is 0. When p is 0, the branch on the long acyl chain is an acetyl group.

In the aspect that step (3b) is performed, namely the unsaturated long acyl group is reacted with a carboxylic acid of the formula

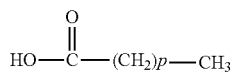

to provide a branched long acyl group of the formula

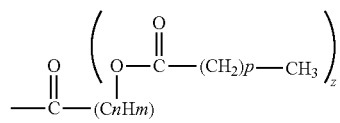

the carboxylic acid will be selected to provide the desired branched long acyl group. As p is from 0 to 4, suitable carboxylic acids for use in the present invention are ethanoic acid (p=0), propanoic acid (p=1), butanoic acid (p=2), pentanoic acid (p=3) and hexanoic acid (p=4).

The value of q, which denotes the length of short acyl chain may be chosen as required. In a preferred aspect q is 0 to 3. In a highly preferred aspect q is 0 or 1. In a further highly preferred aspect q is 0. When q is 0, the short acyl group is an acetyl group.

The value of x, which denotes the number of —OH groups on the unsaturated long acyl group may be chosen as required. In a preferred aspect x is 0 or 1. Preferably x is 0.

The value of y, which denotes the number of —OH groups on the hydroxy long acyl group may be chosen as required. In a preferred aspect y is 1 or 2. Preferably y is 1.

The value of z, which denotes the number of branch groups on the branched long acyl group may be chosen as required. In a preferred aspect z is 1 or 2. Preferably z is 1.

It will be understood by one skilled in the art that the x allows for OH groups to be present or not present on the unsaturated long acyl group. As required by step (3a) of the process the unsaturated long acyl group is hydroxylated to provide the hydroxy long acyl group. By the nature of hydroxylation, at least one OH group must be added to the unsaturated long acyl group to provide the hydroxy long acyl group. Thus when the hydroxy long acyl group has one OH group (i.e. y is 1), this must have been added during the hydroxylation step. When the hydroxy long acyl group has more than one OH groups (e.g. y is 2), one or more of the OH groups may have been present on the unsaturated long acyl group (e.g. x is 1) and the remaining OH groups were added during the hydroxylation step; however, it will be appreciated that alternatively no OH groups may have been was present on the unsaturated long acyl group (i.e. x is 0) and all OH groups were added during the hydroxylation step.

The unsaturated compound of the formula

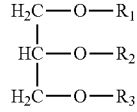

may be obtained or derived from any suitable source. Typically it will be obtained from plant oils. The plant oil may be chosen by one skilled in the art to provide the require unsaturated compound. For example, certain oils will be high in particular unsaturated fatty acids and certain oils will be high in particular —OH containing unsaturated fatty acids. Almost all vegetable oils containing a significant content of unsaturated fatty acids could serve as starting material. For example the unsaturated compound may be derived from sunflower oil, soybean oil, rapeseed (canola) oil, sunflower oil, cottonseed oil, safflower oil, corn oil, peanut oil, mustard seed oil, olive oil, palm oil, rice bran oil, palm kernel oil, moringa oil or mixtures thereof. In one preferred aspect the unsaturated compound is derived from sunflower oil. Preferably the sunflower oil contains oleic acid in an amount of at least 80% by weight based on the total fatty acid content. It will be understood that vegetable oils containing primarily monoenoic fatty acids (oleic, erucic) will derive the monohydroxylated compound (subsequently acetylated), having the —OH (subsequently acyl) group positioned either side of the double bond. The use of oils rich in polyunsaturated fatty acids (linoleic, linolenic) will derive the di- or trihydroxylated compound (subsequently acetylated), having the —OH (subsequently acyl) groups positioned either side of the double bonds. Partially hydrogenated vegetable oils can also be used in this process.

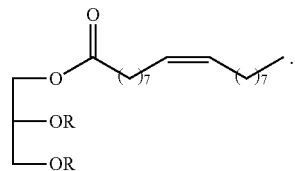

Containing oleic acid

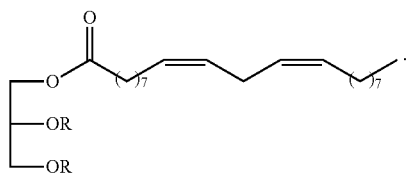

Containing linoleic acid

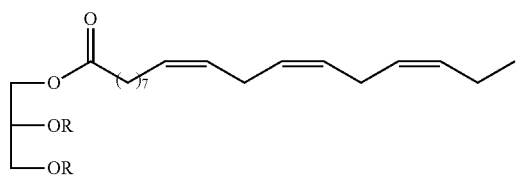

Containing linolenic acid

R = H, acyl

Glycerides Based on Common Unsaturated Fatty Acids

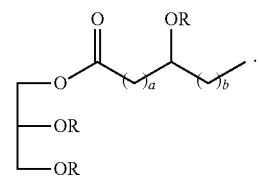

a = 7 or 8
b = 7 or 8
a + b = 15
Based on oleic acid

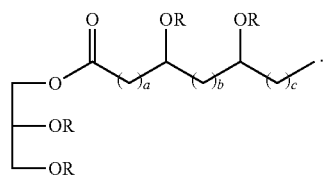

a = 7 or 8
b = 1, 2 or 3
c = 4 or 5
a + b + c = 14
Based on linoleic acid

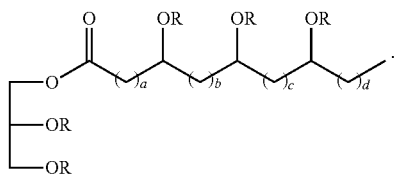

a = 7 or 8
b = 1, 2 or 3
c = 1, 2 or 3
d = 1 or 2
a + b + c + d = 13
Based on linolenic acid R = H, acyl Hydroxylated (Acylated) Glycerides Based on Unsaturated Fatty Acids As will be understood by one skilled in the art, the branch of the branched long acyl group may be placed at any point along the length of the chain of the long acyl group. Indeed it is an advantage of the invention that by selection of the unsaturated compound, and in particular by selection of the point of unsaturation on the unsaturated long acyl group, the position of the branch may be controlled. In a preferred aspect the branched long acyl group is a group of the formula

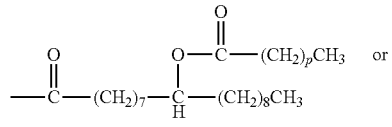

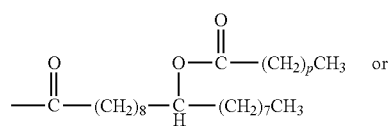

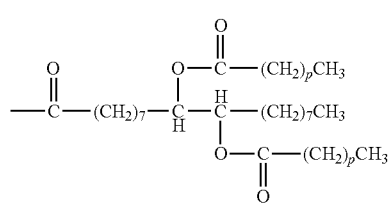

wherein p is from 0 to 4. More preferably the long acyl group is a group of the formula

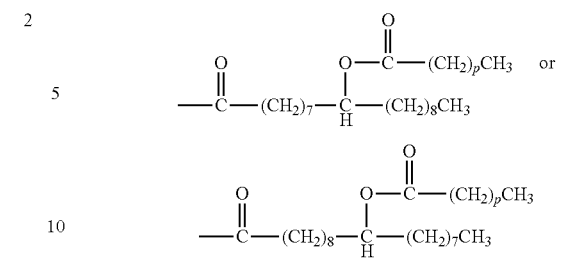

wherein p is from 0 to 4.

In the above aspect p is preferably 0 and thus the branched long acyl group is a group of the formula

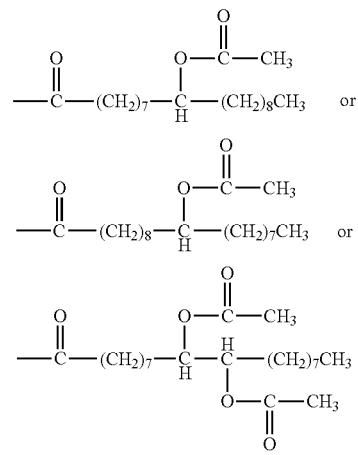

Preferably the branched long acyl group is a group of the formula

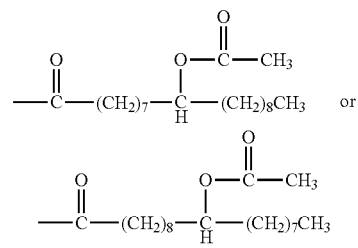

In highly preferred embodiments, the compound is selected from compounds of the formulae

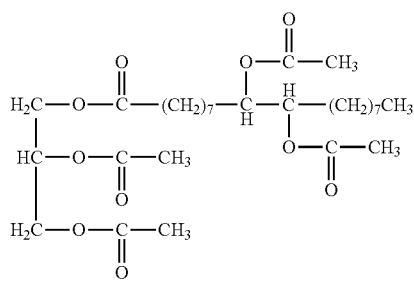

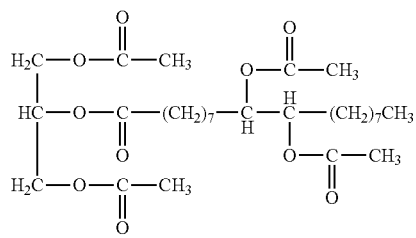
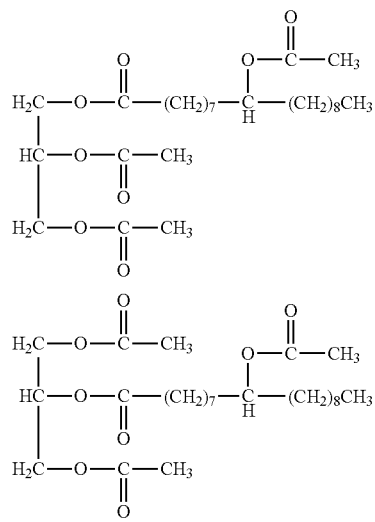
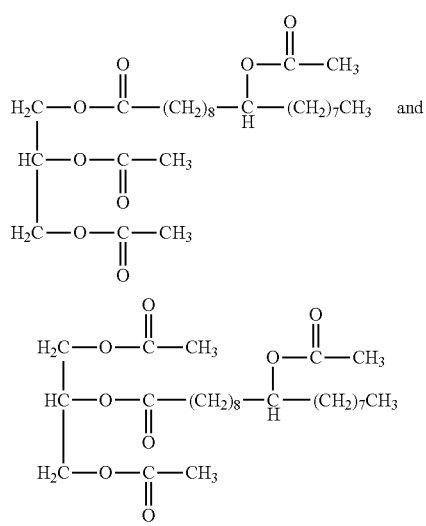
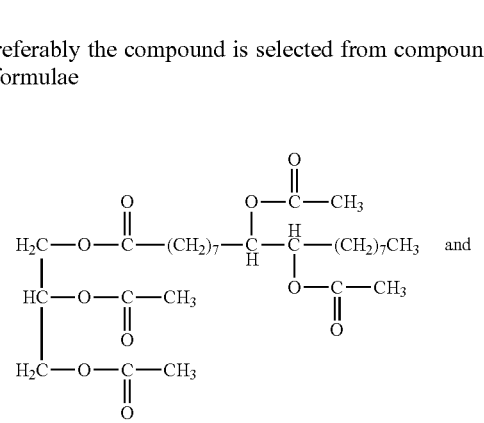
Preferably the compound is selected from compounds of the formulae
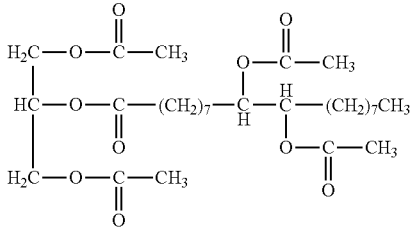
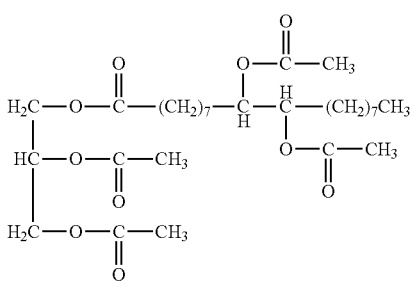
In one aspect the compound is of the formula
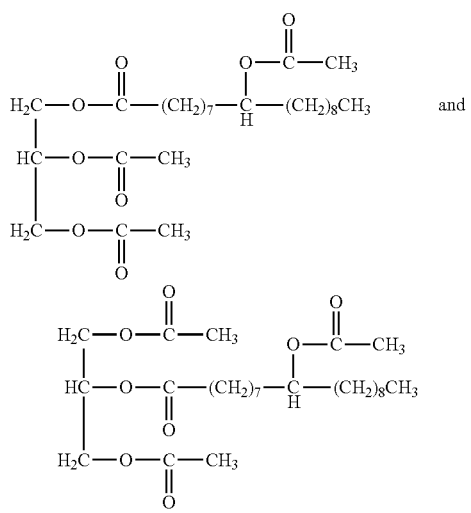
Preferably the compound is selected from compounds of the formulae
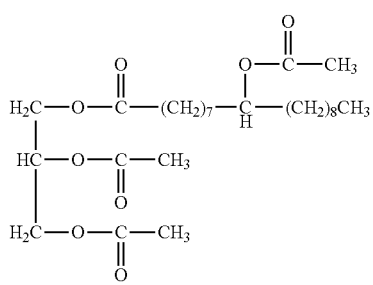
In one aspect the compound is of the formula
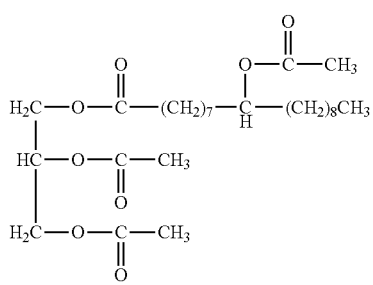
Preferably the compound is selected from compounds of the formulae

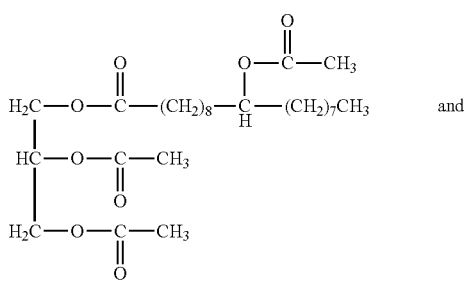

and

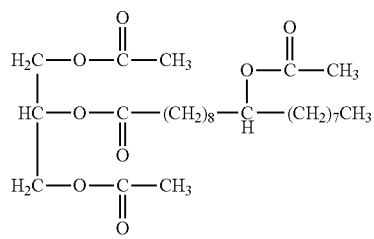

In one aspect the compound is of the formula

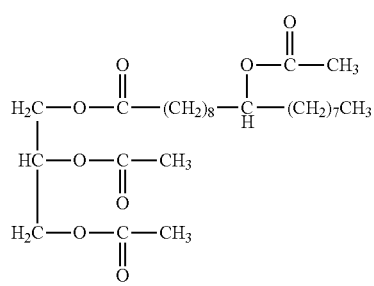

Further Process Steps

It will be understood by one skilled in the art that the process steps described herein are not exhaustive and that the invention may be practices by addition of one or more steps either before the steps recited herein, after the steps recited herein, intermediate to the steps recited herein and combinations thereof. For example the process may comprises a step of protecting any of the hydroxyl groups on the unsaturated compound prior to hydroxylating the unsaturated long acyl group, the process may comprise a step of deprotecting the protected groups after acylation of the hydroxy long acyl group, step (3a)(ii) of the process may comprise acylating the hydroxy long acyl group and acylating other hydroxy groups such that all hydroxy groups on the compound are acylated.

The process may comprise a further step of purifying the reaction product of the present process. This may be for example by fractionation. A typical fractionation step in the process may be performed over a range of 150 to 300° C., more preferably 180 to 250° C., and a pressure of 0.15 to 100 Pa (1 mBar), more preferably 0.15 to 10 Pa. A person skilled in the art will then use routine experiments to select a flow rate that is considered to give an optimal balance between recovery and purity for a particular production run at a particular plant. Suitable processes and process parameter are taught in WO2006/108754.

Polymer Composition

As discussed herein the present invention provides a composition comprising
i) a polymer; and
ii) a compound having the formula

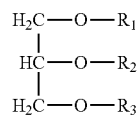

wherein $R_1$, $R_2$ and $R_3$ are independently selected from hydrogen and acyl groups, wherein at least one of $R_1$, $R_2$ and $R_3$ is a branched chain long acyl group of the formula

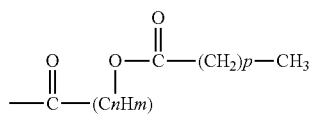

wherein n is from 9 to 21 and m is 2n, and wherein p is from 0 to 4
wherein the other of $R_1$, $R_2$ and $R_3$ are selected from short acyl groups of the formula

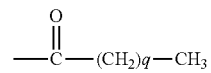

wherein q is from 0 to 4
wherein the compound is obtained or obtainable by a process comprising the steps of:
(1) providing an unsaturated compound having the formula

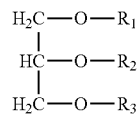

wherein $R_1$, $R_2$ and $R_3$ are independently selected from
  (a) hydrogen,
  (b) unsaturated long acyl group of the formula

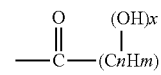

wherein x is from 0 to 3, and wherein n is from 9 to 21 and m is 2n-1-x, 2n-3-x or 2n-5-x; and
  (c) short acyl groups of the formula

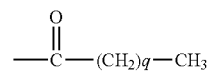

wherein q is from 0 to 4
wherein at least one of $R_1$, $R_2$ and $R_3$ is an unsaturated long acyl group; and
(2) if at least one of $R_1$, $R_2$ and $R_3$ is hydrogen, optionally acylating the compound; and (3a) (i) hydroxylating the unsaturated long acyl group, to provide a hydroxy long acyl group of the formula

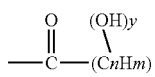

wherein y is from 1 to 4, n is from 9 to 21 and m is 2n+1−y, 2n−1−y or 2n−3−y, and
(ii) acylating the hydroxy long acyl group to provide a branched long acyl group of the formula

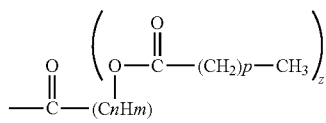

wherein z is from 1 to 4, n is from 9 to 21 and m is 2n+1−z, 2n−1−z or 2n−3−z, and wherein p is from 0 to 4;
or
(3b) reacting the unsaturated long acyl group with a carboxylic acid of the formula

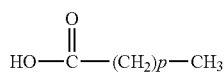

to provide a branched long acyl group of the formula

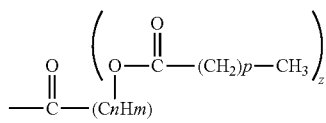

wherein z is from 1 to 4, n is from 9 to 21 and m is 2n+1−z, 2n−1−z or 2n−3−z, and wherein p is from 0 to 4.

As discussed herein the present invention further provides a composition comprising
i) a polymer; and
ii) a compound selected from compounds of the formulae

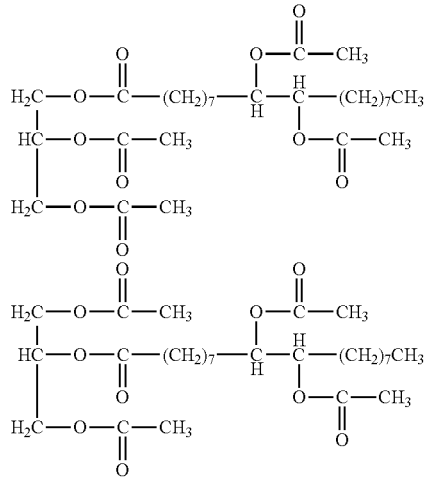

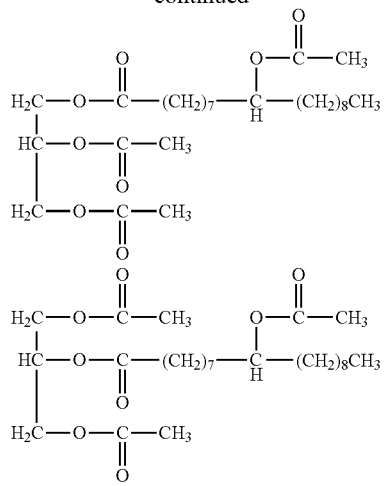

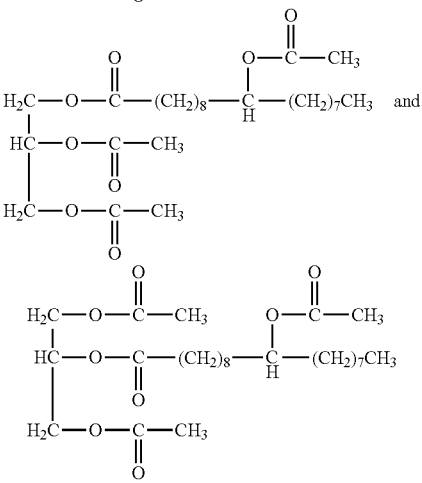 and (iii) optionally, a compound of the formula

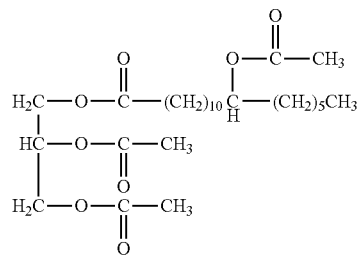

In a preferred aspect the polymer is a thermoplastic polymer. Preferably the thermoplastic polymer is or comprises a vinyl chloride polymer or a vinyl chloride copolymer selected from vinyl chloride/vinyl acetate copolymer, vinyl chloride/vinylidene chloride copolymer, vinyl chloride/ethylene copolymer and a copolymer prepared by grafting vinyl chloride onto ethylene/vinyl acetate copolymer, and mixtures thereof.

In a preferred aspect the thermoplastic polymer is or comprises a polymer blend of a thermoplastic polymer, preferably a thermoplastic polymer as defined above, and a second polymer. Preferably, the second polymer is a methacryl polymer or an acrylonitrile-butadiene-styrene polymer.

The compositions of the present invention may be formulated in any manner to provide the required properties of the composition. In a particular aspect the composition of the present invention comprises the compound in an amount of 0.01 to 200 parts by weight per 100 parts by weight of the polymer, such in an amount of 0.01 to 150 parts by weight per 100 parts by weight of the polymer, such as in an amount of 1 to 100 parts by weight per 100 parts by weight of the polymer, such as in an amount of 10 to 100 parts by weight per 100 parts by weight of the polymer, such as in an amount of 20 to 80 parts by weight per 100 parts by weight of the polymer, such as in an amount of 30 to 80 parts by weight per 100 parts by weight of the polymer, such as in an amount of 40 to 80 parts by weight per 100 parts by weight of the polymer, such as in an amount of 50 to 80 parts by weight per 100 parts by weight of the polymer, such as in an amount of 60 to 70 parts by weight per 100 parts by weight of the polymer.

In one aspect the present invention provides a composition comprising a compound as defined above and an aliphatic polyester. Preferably the aliphatic polyester is biodegradable.

By biodegradable it is meant that a material may be decomposed by indigenous or exogenous organisms, or their enzymes, often in combination with natural weathering and oxidation or reduction processes.

In one aspect the composition may comprise any biodegradable polymer in particle or complete replacement of the aliphatic polyester. Thus in one aspect the present invention provides:
a composition comprising
i) a biodegradable polymer
ii) (a) a compound obtained by the process of the present invention; or
(b) a compound obtainable by the process of the present invention; or
(c) a compound as defined herein, such as a compound selected from compounds of the formulae

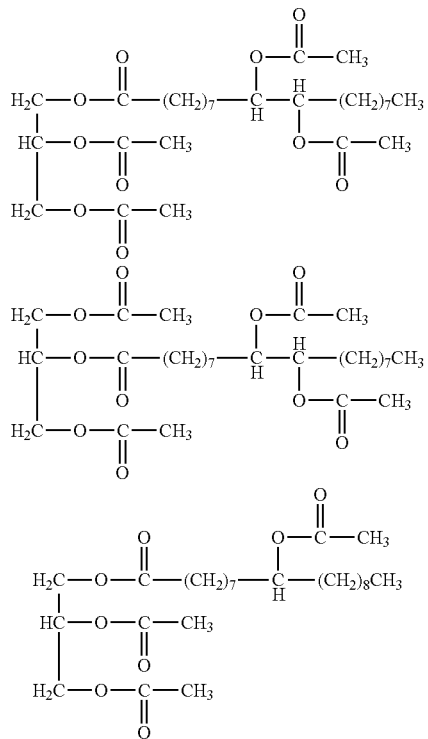

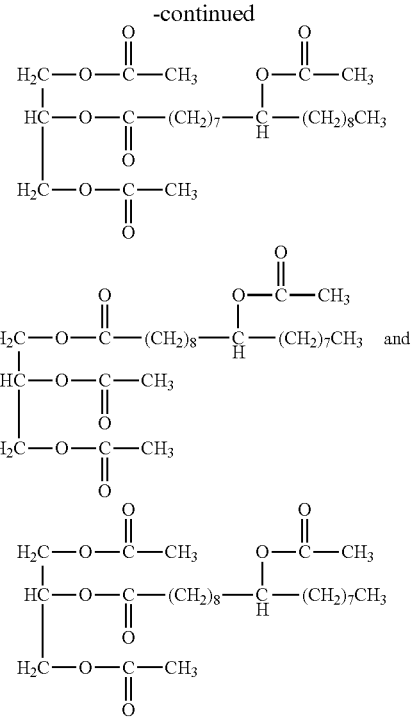

Details of suitable biodegradable polymers can be found in the publication "Biodegradable Plastics—Developments and Environmental Impacts", October 2002, by Australian Government Department of the Environment and Heritage (a copy of which can be found at http://www.deh.gov.au/settlements/publications/waste/degradables/biodegradable/chapter3.html)

The present composition may be subject to bioremediation. Bioremediation is the deliberate use of these processes of biodegradation in order to return an environment altered by contaminants to its original condition. This is less expensive or problematic than searching for and possibly excavating the contaminant, followed either by disposal elsewhere, or incineration.

Preferably the polymer is a plastic polymer. By plastic it is typically meant a material that is capable of flowing under heat and/or pressure and then subsequently setting.

As discussed in EP1029890 suitable aliphatic polyesters for use used in the present invention include an aliphatic polyester comprising a lactic acid unit in the molecule. Specific examples thereof include (1) polylactic acid, and lactic acid-other aliphatic hydroxycarboxylic acid copolymers, (2) aliphatic polyesters comprising polyfunctional polysaccharides and a lactic acid unit, (3) aliphatic polyesters comprising an aliphatic polyvalent carboxylic acid unit, an aliphatic polyvalent alcohol unit and a lactic acid unit, and (4) mixtures thereof. Namely, examples thereof include the lactic acid-based polymers (1) to (4). Among them, polylactic acid, and lactic acid-other aliphatic hydroxycarboxylic acid copolymers may be used. Preferable still is polylactic acid.

Lactic acid includes a L-lactic acid and a D-lactic acid. When referred to simply as lactic acid in the present invention, both the L-lactic acid and D-lactic acid are indicated unless otherwise stated. The molecular weight of a polymer indicates the weight-average molecular weight unless otherwise stated. As the polylactic acid used in the present invention, there are listed poly(L-lactic acid) solely composed of L-lactic acid, poly(D-lactic acid) solely composed of D-lactic acid, poly(DL-lactic acid) comprising a L-lactic acid unit and a D-lactic acid unit in various proportions, and the like. As the hydroxycarboxylic acid of a lactic acid-other aliphatic hydroxycarboxylic acid copolymer, there are listed glycolic acid, 3-hydroxybutyric acid, 4-hydroxybutyric acid, 4-hydroxyvaleric acid, 5-hydroxyvaleric acid, 6-hydroxycaproic acid and the like.

Use of the polymers such as lactic acid based polymers allows for the provision of polymers systems in which the constituent materials are not obtained from (or are obtained to a lesser extent from) fossil fuels e.g. crude oil. Thus these polymer systems are bio-sustainable.

As the method for producing polylactic acid used in the present invention, a method in which L-lactic acid, D-lactic acid or DL-lactic acid is directly dehydrated and poly-condensed, a method in which a lactide, cyclic dimer of such lactic acid is ring opening-polymerized, and the like are listed. The ring opening polymerization may also be conducted in the presence of a compound having a hydroxyl group such as higher alcohol, hydroxycarboxylic acid and the like. The compound may be produced by any method. As the method for producing a lactic acid-other aliphatic hydroxycarboxylic acid copolymer, a method in which the above-described lactic acid and the above-described aliphatic hydroxycarboxylic acid are dehydrated and polycondensed, a method in which a lactide, cyclic dimer of the above-described lactic acid, and a cyclic body of the above-described hydroxycarboxylic acid are ring opening-copolymerized, and the like are listed. The copolymer may be produced by any method. The amount of a lactic acid unit contained in a lactic acid-other aliphatic hydroxycarboxylic acid copolymer is preferably at least 40 mol %.

Examples of polyfunctional polysaccharides used for producing an aliphatic polyester comprising polyfunctional polysaccharides and a lactic acid unit include cellulose, cellulose acetate, cellulose nitrate, methyl cellulose, ethyl cellulose, celluloid, viscose rayon, regenerated cellulose, cellophane, cupra, cupro-ammonium rayon, cuprofan, bemberg, hemicellulose, starch, acropectin, dextrin, dextran, glycogen, pectin, chitin, chitosan, gum arabic, cyamoposis gum, locust bean gum, acacia gum and the like, and mixtures, and derivatives. Among them, cellulose acetate and ethyl cellulose are preferable.

As the method for producing an aliphatic polyester comprising polyfunctional polysaccharides and a lactic acid unit, a method in which the above-described polysaccharides are reacted with the above-described polylactic acid, lactic acid-other aliphatic hydroxycarboxylic acid copolymer and the like, a method in which the above-described polysaccharides are reacted with the above-described lactic acid, cyclic esters and the like, as well as other methods are listed. The aliphatic polyester may be produced by any method. It is preferable that the amount of a lactic acid unit contained in the aliphatic polyester is at least 50 mol %.

Examples of the aliphatic polyvalent carboxylic acid used for producing an aliphatic polyvalent carboxylic acid unit, an aliphatic polyvalent alcohol unit and a lactic acid unit include oxalic acid, succinic acid, malonic acid, glutaric acid, adipic acid, pimelic acid, suberic acid, azelaic acid, undecanedioic acid, dodecanedioic acid and the like, and anhydrides thereof. These may be mixed with an acid anhydride. Examples of the aliphatic polyvalent alcohol include ethylene glycol, diethylene glycol, triethylene glycol, propylene glycol, dipropylene glycol, 1,3-butanediol, 1,4-butanediol, 3-methyl-1,5-pentanediol, 1,6-hexanediol, 1,9-nonanediol, neopentyl glycol, tetramethylene glycol, 1,4-cyclohexanedimethanol and the like.

As the method for producing an aliphatic polyester comprising an aliphatic polyvalent carboxylic acid unit, an aliphatic polyvalent alcohol unit and a lactic acid unit, a method in which the above-described aliphatic polyvalent carboxylic acid and the above-described aliphatic polyvalent alcohol are reacted with the above-described polylactic acid, lactic acid-other aliphatic hydroxycarboxylic acid copolymer and the like, a method in which the above-described aliphatic polyvalent carboxylic acid and the above-described aliphatic polyvalent alcohol are reacted with the above-described polylactic acid, cyclic esters and the like, as well as other methods are listed. The aliphatic polyester may be produced by any method. It is preferable that the amount of a lactic acid unit contained in the aliphatic polyester is at least 50 mol %.

If it is desired that a film be prepared from the present composition, the molecular weight of the aliphatic polyester exerts an influence on processability into a film, and strength and degradability of the obtained film. When the molecular weight is low, strength of the obtained film decreases and the film may be broken in use. Further, degradation speed increases. On the other hand, when the molecular weight is high, processability lowers and film moulding becomes difficult. From such a standpoint, the molecular weight of the aliphatic polyester is in a range from about 10,000 to about 1,000,000. A further preferable range is from 100,000 to 300,000.

The compound described herein may be used in polymers as a plasticiser. In an alternative application, the compound described herein may be used in polymers as an impact modifier. Thus in one aspect, the present invention provides a plasticiser comprising (a) a compound obtained by the process of the present invention; or (b) a compound obtainable by the process of the present invention; or (c) a compound as defined herein, such as a compound selected from compounds of the formulae

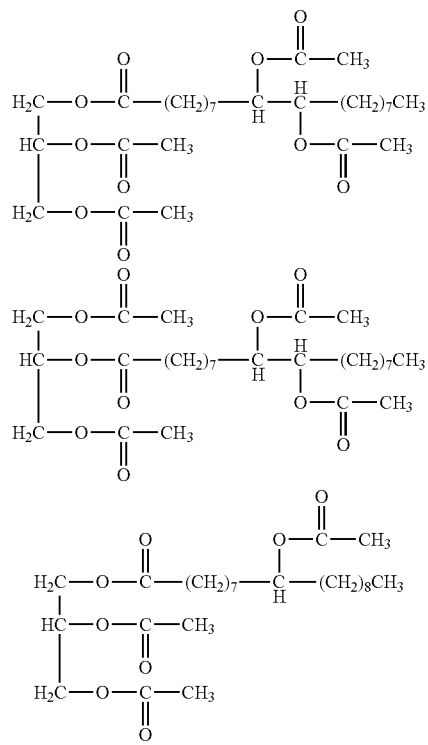

-continued

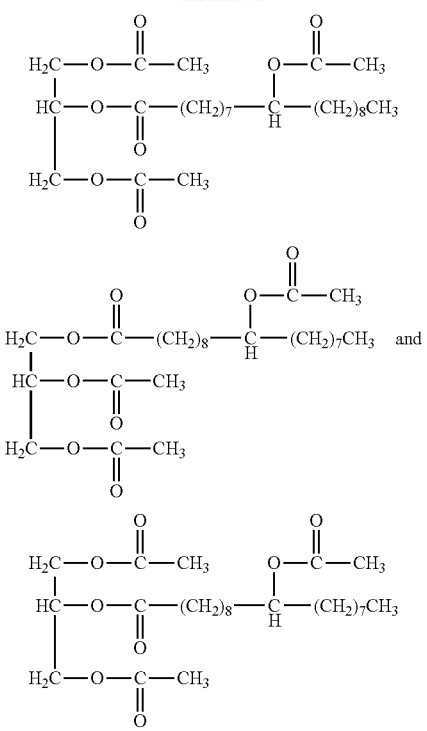

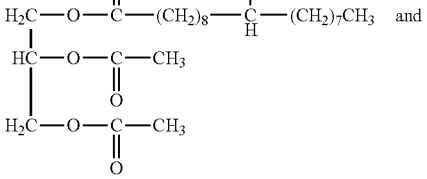

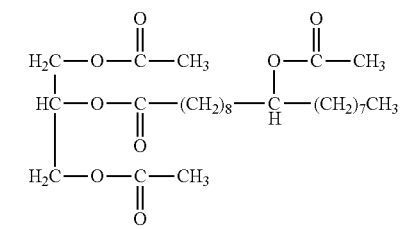

In a further aspect, the present invention provides an impact modifier comprising (a) a compound obtained by the process of the present invention; or (b) a compound obtainable by the process of the present invention; or (c) a compound as defined herein, such as a compound selected from compounds of the formulae

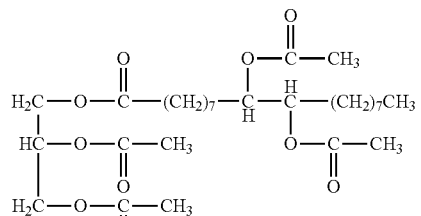

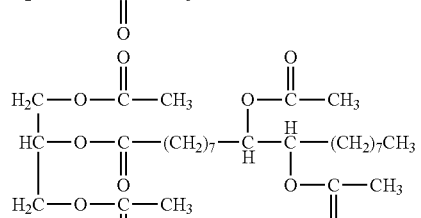

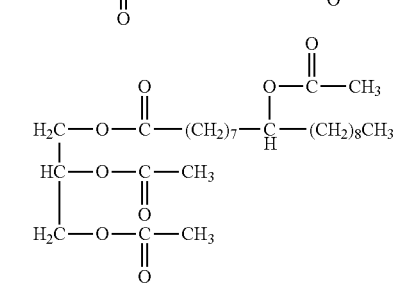

-continued

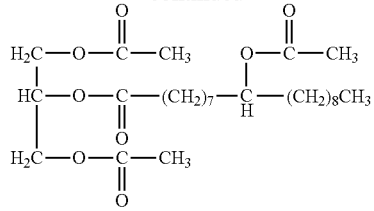

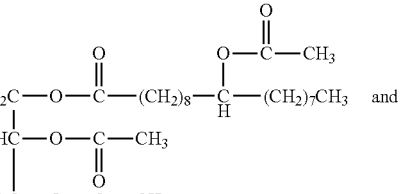

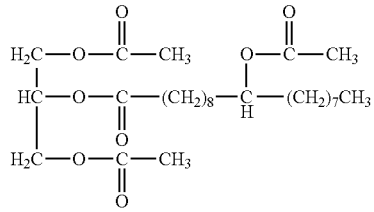

The invention will now be described in further detail with in the following Examples.

EXAMPLES

Synthesis of Monoglyceride

All reactions are performed under $N_2$ atmosphere. 2000 g triglyceride is added into a reactor together with 700 g glycerol and 0.1% basic catalyst. The reaction mixture is heated to 250° C. under stirring until it appears homogeneous. After an additional 30 minutes, the reaction mixture is cooled to ca. 100° C. and the excess glycerol removed under vacuum. The monoglyceride is removed from the reaction mixture by short path distillation. The purity of the monoglyceride is determined by the standard measures of gas chromatography (GC), OH-value and acid-value.

Synthesis of Acetylated Monoglyceride

All reactions are performed under $N_2$ atmosphere. 500 g monoglyceride is charged into the reactor and heated to 100° C. 350 g acetic anhydride is added under stirring. As this reaction is exothermic, the addition of acetic anhydride is performed carefully. The reaction mixture is heated to reflux and after 60 minutes the acetic acid and excess acetic anhydride is removed by distillation and vacuum distillation. The crude reaction mixture is cooled to 100° C., desodorized and purified by short path distillation. The purity of the acetylated monoglyceride is determined by the standard measures GC, OH-value and acid-value.

Preparation of Mono-Hydroxy and Mono Acetylated Product 440 g (1 mol) fully acetylated monooleate is dissolved in 750 ml dry THF. 500 ml of a 1 M solution of borane in THF is added in 60 minutes with good stirring in an inert atmosphere. The reaction mixture is held below 20° C. by cooling with a water bath.

The mixture is stirred at room temperature another 3 hours and the reaction quenched with drop wise addition of methanol. After the $H_2$ evolution stopped, 160 ml 3M NaOH-solution is added, followed by 108 ml 50% $H_2O_2$ solution, thereby keeping the temperature under 35° C. The mixture is stirred for another hour and 500 ml water is added. The aqueous phase is removed and the organic phase washed several times with a saturated NaCl solution. The organic phase is dried with NaSO$_4$ and the solvent removed in vacuo. The product is analyzed and identified by GC, mass spectrometry (MS), acid number and OH-value.

The hydroxyl compound is acetylated with an excess (1.5 eq.) acetic anhydride at 90-130° C. After the reaction is complete (ca. 1-2 hours), acetic acid and excess acetic anhydride is removed in vacuo. The liquid product is analyzed and characterized by GC/MS, acid number and OH-number.

Identification of the Reaction Product, SOSAR SEL 3568:

The combined yield of this two-step synthesis is >90%. The product is denoted herein as SOSAR SEL 3568. SOSAR SEL 3568 was found to comprise a mixture of 9- and 10-acetoxy-octadecanoic acid 2,3-diacetoxypropyl ester (M=500.67), namely

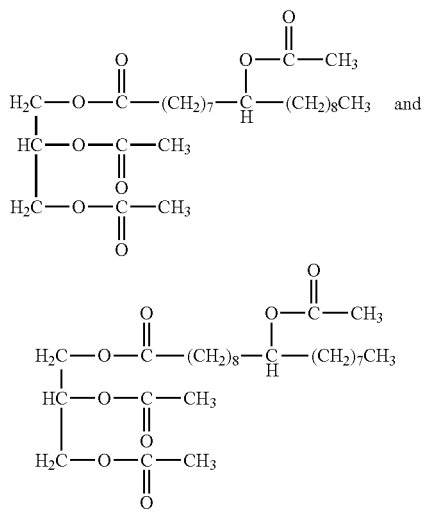

The verification is based on the comparison with 12-acetoxy-octadecanoic acid 2,3-diacetoxypropyl ester (Soft-N-Safe). The main peak in SOSAR SEL 3568 consists of 2 coeluting component pairs (containing also the 1,3-diacetoxypropyl esters).

The MS shows the same main fragments compared to Soft-N-Safe:
m/z=43 (acetoxy-group), m/z=440 (loss of acetic acid), m/z=380 (loss of 2×acetic acid) and m/z=159 (2,3-diacetoxypropyl ester moiety). Additionally the Soft-N-Safe molecule shows m/z=355 (loss of aliphatic chain next to 12-acetoxy group+loss of acetic acid). Similarly, one component pair in SOSAR SEL 3568 shows m/z=313 (loss of aliphatic chain next to 9-acetoxy group+acetic acid), the other m/z=327 (loss of aliphatic chain next to 10-acetoxy group+loss of acetic acid). This fragmentation pattern comes from the 9- and 10-acetoxy-compounds, where m/z=327.

The GC/MS analysis of transesterified SOSAR SEL 3568 (as both ethyl and methyl esters) confirmed the findings and conclusions made from the above experiments.

The reaction product may be further purified. As discussed above, In the present work further purification was performed by short path distillation.

A KD-L5 short path distillation unit was used with the heat transfer fluid adjusted to 215° C. and the condenser to 70° C. The distillation is performed at 4×10$^{-3}$ mbar. The amount of distillate corresponds to a cut of 80% at a flow of 750 g/h.

The distillate is analysed by GC and LC, showing the acylated C-18-OH monoglyceride to be the major component with ca. 84%, the rest being mainly the acylated C-16 and C-18 monoglycerides. A GC-chromatogram of the distilled reaction product can be seen in FIG. 1, together with FIG. 2 which is a chromatogram of a 12-acetoxy-octadecanoic acid 2,3-diacetoxypropyl ester (Soft-N-Safe; SNS) reference sample for comparison.

Synthesis of Dihydroxylated Monoglyceride 150 g monoglyceride (monooleate) is charged into a reactor and heated to 50° C. 10 g formic acid and 70 g 50% hydrogen peroxide solution is added under stirring. The reaction mixture is stirred for another 4 hours. 100 ml cyclohexane is added and the reaction mixture transferred to a separation funnel. The organic layer is washed with aqueous sodium sulfite and demineralized water. The organic layer is separated and the solvent removed in vacuo. The purity of the product is analyzed by GC, I—, OH— and acid value.

The dihydroxyl compound is acetylated as described above. The product is analyzed and characterized by GC/MS, acid number and OH-number. The product is denoted herein as SOSAR MKH 3972. SOSAR MKH 3972 was found to comprise a compound of the formula

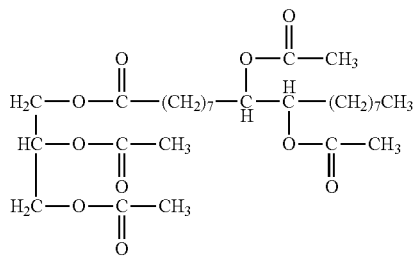

Plasticiser Testing

GRINDSTED SOFT-N-SAFE, SOSAR SEL 3568 and SOSAR MKH 3972 were evaluated in respect of Tensile strength, Modulus and elongation in accordance with DIN 53457 and evaluated in respect of shore A hardness in accordance with DIN 53505.

| Product | Tensile Strength [MPa] | 100% Modulus [MPa] | Elongation at break [%] | Shore A at 15 sec. |
|---|---|---|---|---|
| GRINDSTED SOFT-N-SAFE | 18.0 | 4.4 | 794 | 77.7 |
| SOSAR SEL 3568 | 18.7 | 4.5 | 828 | 78.2 |
| SOSAR MKH 3972 | 21.6 | 5.6 | 815 | 80.7 |

GRINDSTED SOFT-N-SAFE is a compound of the formula shown below and is available from Danisco A/S, Denmark

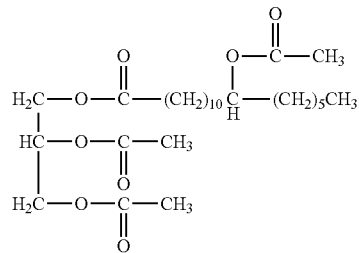

It was found that SOSAR SEL 3568 is an efficient plasticiser and has mechanical properties tested to be very comparable to GRINDSTED SOFT-N-SAFE.

SOSAR MKH 3972 also performed as a plasticiser.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A process for the preparation of a compound having the formula

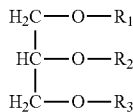

wherein $R_1$, $R_2$ and $R_3$ are independently selected from hydrogen and acyl groups, wherein at least one of $R_1$, $R_2$ and $R_3$ is a branched chain long acyl group of the formula

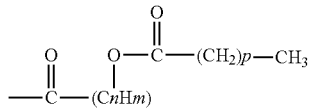

wherein n is from 9 to 21 and m is 2n, and wherein p is from 0 to 4, wherein the other of $R_1$, $R_2$ and $R_3$ are selected from short acyl groups of the formula

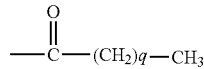

wherein q is from 0 to 4,
the process comprising the steps of:
(1) providing an unsaturated compound having the formula

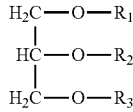

wherein $R_1$, $R_2$ and $R_3$ are independently selected from
(a) hydrogen,
(b) unsaturated long acyl group of the formula

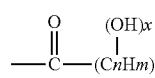

wherein x is from 0 to 3, and wherein n is from 9 to 21 and m is 2n−1−x, 2n−3−x or 2n−5−x; and (c) short acyl groups of the formula

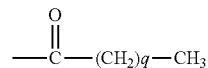

wherein q is from 0 to 4,
wherein at least one of $R_1$, $R_2$ and $R_3$ is an unsaturated long acyl group; and
(2) if at least one of $R_1$, $R_2$ and $R_3$ is hydrogen, optionally acylating the compound; and
(3a) (i) hydroxylating the unsaturated long acyl group, to provide a hydroxy long acyl group of the formula

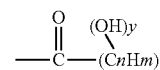

wherein y is from 1 to 4, n is from 9 to 21 and m is 2n+1−y, 2n−1−y or 2n−3−y, and
(ii) acylating the hydroxy long acyl group to provide a branched long acyl group of the formula

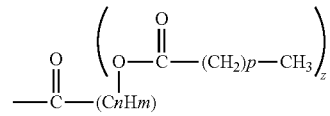

wherein z is from 1 to 4, n is from 9 to 21 and m is 2n+1−z, 2n−1−z or 2n−3−z, and wherein p is from 0 to 4;
or
(3b) reacting the unsaturated long acyl group with a carboxylic acid of the formula

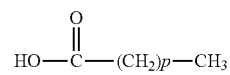

to provide a branched long acyl group of the formula

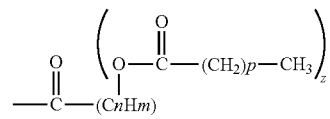

wherein z is from 1 to 4, n is from 9 to 21 and m is 2n+1−z, 2n−1−z or 2n−3−z, and wherein p is from 0 to 4.

2. A process according to claim 1 wherein step (3a) is performed.

3. A process according to claim 1 wherein the unsaturated long acyl group of the formula

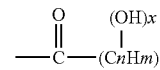

wherein x is from 0 to 3, n is from 9 to 21 and m is 2n−1.

4. A process according to claim 1 wherein the hydroxy long acyl group of the formula

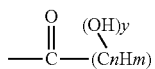

wherein y is from 1 to 4, n is from 9 to 21 and m is 2n.

5. A process according to claim 1 for the preparation of a compound having the formula

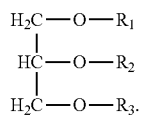

wherein two of $R_1$, $R_2$ and $R_3$ are the short acyl groups and one of $R_1$, $R_2$ and $R_3$ is a branched long acyl group.

6. A process according to claim 1 wherein n is from 13 to 19.

7. A process according to claim 6 wherein n is from 15 to 19.

8. A process according to claim 6 wherein n is 17.

9. A process according claim 1 wherein p is 0 to 3.

10. A process according to claim 9 wherein p is 0.

11. A process according to claim 1 wherein q is 0 to 3.

12. A process according to claim 9 wherein q is 0.

13. A process according to claim 1 wherein x is 0.

14. A process according to claim 1 wherein y is 1.

15. A process according to claim 1 wherein z is 1.

16. A process according to claim 1 wherein the unsaturated compound is derived from sunflower oil, soybean oil, rapeseed (canola) oil, sunflower oil, cottonseed oil, safflower oil, corn oil, peanut oil, mustard seed oil, olive oil, palm oil, rice bran oil, palm kernel oil, moringa oil or mixtures thereof.

17. A process according to claim 16 wherein the sunflower oil contains oleic acid in an amount of at least 80% by weight based on the total fatty acid content.

18. A process according to claim 1 wherein the branched long acyl group is a group of the formula

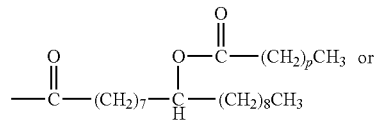

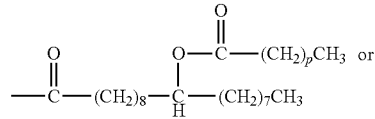

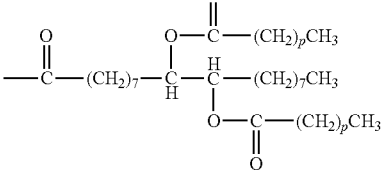

wherein p is from 0 to 4.

19. A process according to claim 1 wherein the branched long acyl group is a group of the formula

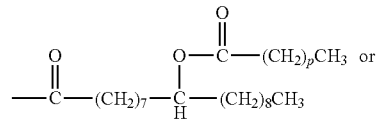

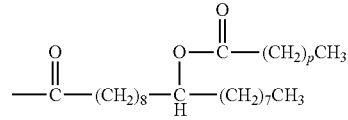

wherein p is from 0 to 4.

20. A process according to claim 1 wherein the branched long acyl group is a group of the formula

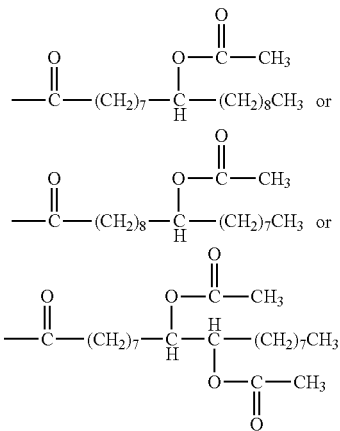

wherein p is from 0 to 4.

21. A process according to claim 1 wherein the branched long acyl group is a group of the formula

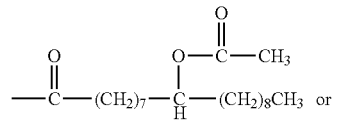

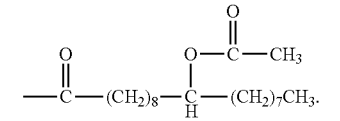

22. A process according to claim 1 for the preparation of a compound having the formula

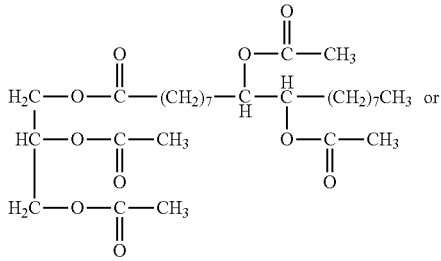

-continued

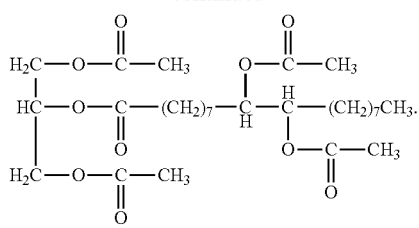

23. A process according to claim 1 for the preparation of a compound having the formula

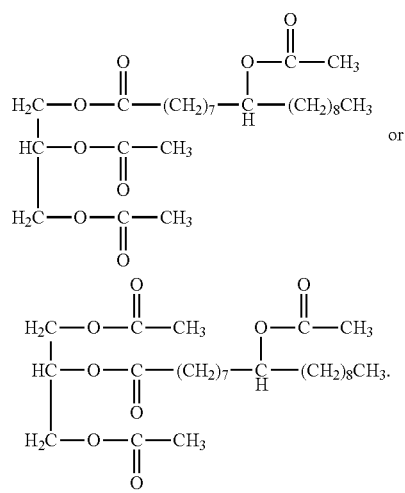

24. A process according to claim 1 for the preparation of a compound having the formula

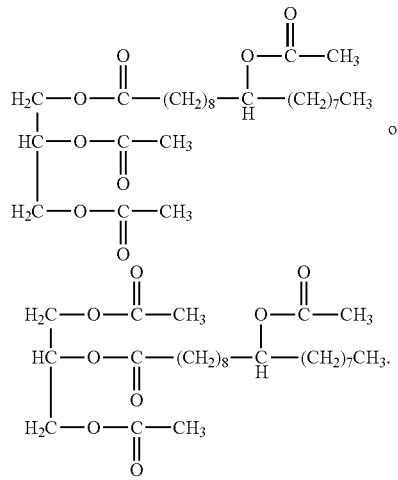

25. A process according to claim 1 wherein the process comprises a step of protecting any hydroxyl groups on the unsaturated compound prior to hydroxylating the unsaturated long acyl group.

26. A process according to claim 25 wherein the process comprises a step of deprotecting the protected groups after acylation of the hydroxy long acyl group.

27. A process according to claim 1 wherein step (3a)(ii) comprises acylating the hydroxy long acyl group and acylating other hydroxy groups such that all hydroxy groups on the compound are acylated.

28. A compound obtained by the process of claim 1.

29. A compound of the formula

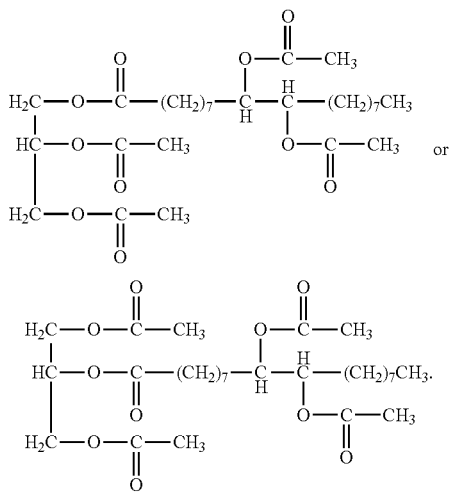

30. A compound of the formula

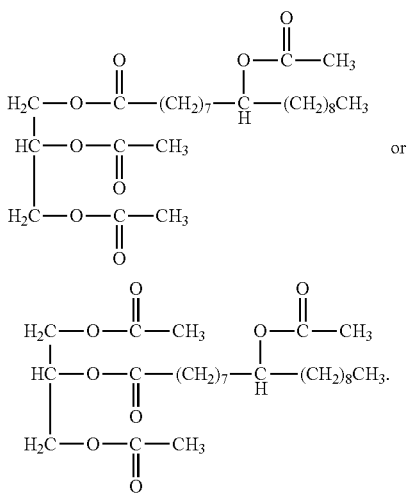

31. A compound of the formula

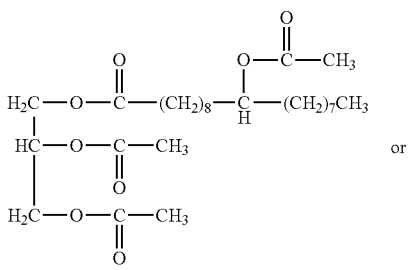

-continued $$\begin{array}{c} \text{H}_2\text{C}-\text{O}-\overset{\overset{\displaystyle O}{\|}}{\text{C}}-\text{CH}_3 \quad \overset{\overset{\displaystyle O}{\|}}{\text{O}-\text{C}-\text{CH}_3} \\ \text{HC}-\text{O}-\overset{}{\text{C}}-(\text{CH}_2)_8-\underset{\text{H}}{\text{C}}-(\text{CH}_2)_7\text{CH}_3. \\ \overset{\|}{\text{O}} \\ \text{H}_2\text{C}-\text{O}-\overset{}{\text{C}}-\text{CH}_3 \\ \overset{\|}{\text{O}} \end{array}$$

32. A composition comprising
i) a compound of the formula $$\begin{array}{c} \overset{\overset{\displaystyle O}{\|}}{\text{O}-\text{C}-\text{CH}_3} \\ \text{H}_2\text{C}-\text{O}-\overset{\overset{\displaystyle O}{\|}}{\text{C}}-(\text{CH}_2)_{10}\underset{\text{H}}{\text{C}}-(\text{CH}_2)_5\text{CH}_3 \\ \text{HC}-\text{O}-\text{C}-\text{CH}_3 \\ \overset{\|}{\text{O}} \\ \text{H}_2\text{C}-\text{O}-\text{C}-\text{CH}_3 \\ \overset{\|}{\text{O}} \end{array}$$

and
ii) a compound according to claim 28.

33. A composition comprising
i) a polymer AND
ii) a compound according to claim 28.

34. A composition according to claim 33 wherein the polymer is a thermoplastic polymer.

35. A composition according to claim 34 wherein the thermoplastic polymer is or comprises a vinyl chloride polymer or a vinyl chloride copolymer selected from vinyl chloride/vinyl acetate copolymer, vinyl chloride/vinylidene chloride copolymer, vinyl chloride/ethylene copolymer and a copolymer prepared by grafting vinyl chloride onto ethylene/vinyl acetate copolymer, and mixtures thereof.

36. A composition according to claim 33 wherein the polymer is a biodegradable polymer.

37. A composition comprising
i) a compound of the formula $$\begin{array}{c} \overset{\overset{\displaystyle O}{\|}}{\text{O}-\text{C}-\text{CH}_3} \\ \text{H}_2\text{C}-\text{O}-\overset{\overset{\displaystyle O}{\|}}{\text{C}}-(\text{CH}_2)_{10}\underset{\text{H}}{\text{C}}-(\text{CH}_2)_5\text{CH}_3 \\ \text{HC}-\text{O}-\text{C}-\text{CH}_3 \\ \overset{\|}{\text{O}} \\ \text{H}_2\text{C}-\text{O}-\text{C}-\text{CH}_3 \\ \overset{\|}{\text{O}} \end{array}$$

and
ii) a compound according to claim 29.

38. A composition comprising
i) a compound of the formula $$\begin{array}{c} \overset{\overset{\displaystyle O}{\|}}{\text{O}-\text{C}-\text{CH}_3} \\ \text{H}_2\text{C}-\text{O}-\overset{\overset{\displaystyle O}{\|}}{\text{C}}-(\text{CH}_2)_{10}\underset{\text{H}}{\text{C}}-(\text{CH}_2)_5\text{CH}_3 \\ \text{HC}-\text{O}-\text{C}-\text{CH}_3 \\ \overset{\|}{\text{O}} \\ \text{H}_2\text{C}-\text{O}-\text{C}-\text{CH}_3 \\ \overset{\|}{\text{O}} \end{array}$$

and
ii) a compound according to claim 30.

39. A composition comprising
i) a compound of the formula $$\begin{array}{c} \overset{\overset{\displaystyle O}{\|}}{\text{O}-\text{C}-\text{CH}_3} \\ \text{H}_2\text{C}-\text{O}-\overset{\overset{\displaystyle O}{\|}}{\text{C}}-(\text{CH}_2)_{10}\underset{\text{H}}{\text{C}}-(\text{CH}_2)_5\text{CH}_3 \\ \text{HC}-\text{O}-\text{C}-\text{CH}_3 \\ \overset{\|}{\text{O}} \\ \text{H}_2\text{C}-\text{O}-\text{C}-\text{CH}_3 \\ \overset{\|}{\text{O}} \end{array}$$

and
ii) a compound according to claim 31.

40. A composition comprising
i) polymer and
ii) a compound according to claim 29.

41. A composition comprising
i) polymer and
ii) a compound according to claim 30.

42. A composition comprising
i) polymer and
ii) a compound according to claim 31.

43. A composition comprising
i) polymer and
ii) a composition according to claim 32.

* * * * *